(12) United States Patent
Batarilo et al.

(10) Patent No.: US 12,415,029 B2
(45) Date of Patent: Sep. 16, 2025

(54) FLUID DELIVERY SYSTEM

(71) Applicant: ACIST MEDICAL SYSTEMS INC., Eden Prairie, MN (US)

(72) Inventors: Zvonimir Batarilo, Lausanne (CH); Dieter Heidmann, Geretsried (DE); Jan Sievertsen, Munich (DE)

(73) Assignee: ACIST MEDICAL SYSTEMS INC., Eden Prairie, MN (US)

( * ) Notice: Subject to any disclaimer, the term of this patent is extended or adjusted under 35 U.S.C. 154(b) by 735 days.

(21) Appl. No.: 17/787,641

(22) PCT Filed: Sep. 10, 2020

(86) PCT No.: PCT/EP2020/075268
§ 371 (c)(1),
(2) Date: Jun. 21, 2022

(87) PCT Pub. No.: WO2021/129958
PCT Pub. Date: Jul. 1, 2021

(65) Prior Publication Data
US 2022/0409808 A1    Dec. 29, 2022

(30) Foreign Application Priority Data
Dec. 23, 2019 (EP) .................................... 19219192

(51) Int. Cl.
*A61M 5/145* (2006.01)
*A61M 5/00* (2006.01)
(Continued)

(52) U.S. Cl.
CPC ........ *A61M 5/14216* (2013.01); *A61M 5/007* (2013.01); *A61M 5/145* (2013.01); *A61M 5/16804* (2013.01)

(58) Field of Classification Search
CPC .............. A61M 5/007; A61M 5/14216; A61M 5/1422; A61M 5/145; A61M 5/1452;
(Continued)

(56) References Cited

U.S. PATENT DOCUMENTS 4,065,230 A * 12/1977 Gezari ................ A61M 5/1422
604/152
4,674,317 A * 6/1987 Cohrs ..................... G01F 25/11
73/1.21
(Continued)

FOREIGN PATENT DOCUMENTS

DE       102011120105 A1    6/2013
EP           1035882 B1    6/2004
(Continued)

OTHER PUBLICATIONS

International Search Report and Written Opinion for PCT/EP2020/075268, mailed Oct. 1, 2020.

*Primary Examiner* — Benjamin J Klein
(74) *Attorney, Agent, or Firm* — VIVICAR Law, PLLC

(57) ABSTRACT

A fluid delivery system is disclosed which comprises at least one supply station for supplying at least one fluid, a pressurizing unit for pressurizing said at least one fluid, an inlet fluid circuit in fluid communication with said at least one supply station and with a pump module of said pressurizing unit and an outlet fluid circuit in fluid communication with said pump module for discharging the fluid from the chamber. The chamber is provided with a piston reciprocating therein, thereby defining first and second variable-volume sub-chambers. The fluid delivery system further comprises a recirculation fluid circuit fluidically connecting said first and second variable-volume sub-chambers, and an actuator associated to said recirculation fluid circuit for managing the passage of said at least one fluid between said first and
(Continued)

second variable-volume sub-chambers in both directions. A method of operating the fluid delivery system is also disclosed.

12 Claims, 8 Drawing Sheets

(51) Int. Cl.
    *A61M 5/142*     (2006.01)
    *A61M 5/168*     (2006.01)

(58) Field of Classification Search
    CPC .......... A61M 5/16804; A61M 5/16809; A61M 5/16813; A61M 2005/1402; A61M 2205/3379
    See application file for complete search history.

(56) References Cited

U.S. PATENT DOCUMENTS

| | | | |
|---|---|---|---|
| 5,111,682 A * | 5/1992 | Halpin | G01F 25/11 |
| | | | 73/1.19 |
| 5,411,374 A | 5/1995 | Gram | |
| 5,551,488 A | 9/1996 | Gram | |
| 6,135,719 A | 10/2000 | Yoder et al. | |
| 7,934,413 B2 * | 5/2011 | Winchester | G01F 25/13 |
| | | | 73/1.21 |
| 7,963,422 B2 * | 6/2011 | Ramnarine | F04B 13/00 |
| | | | 222/77 |
| 9,925,331 B2 * | 3/2018 | Uber, III | A61M 5/007 |
| 2007/0196219 A1 | 8/2007 | Hofling et al. | |
| 2010/0170512 A1 * | 7/2010 | Kuypers | A61M 16/0069 |
| | | | 128/204.23 |
| 2012/0053557 A1 | 3/2012 | Abal | |
| 2021/0169743 A1 * | 6/2021 | Nadermanesh | A61M 1/81 |
| 2023/0011814 A1 | 1/2023 | Batarilo et al. | |
| 2023/0084243 A1 | 3/2023 | Batarilo et al. | |

FOREIGN PATENT DOCUMENTS

| | | | |
|---|---|---|---|
| WO | 9015632 A1 | 12/1990 | |
| WO | WO-2008126035 A1 * | 10/2008 | ............. F04B 15/02 |
| WO | 2015084302 A1 | 6/2015 | |
| WO | 2016033351 A2 | 3/2016 | |
| WO | 2017114706 A1 | 7/2017 | |

* cited by examiner

FLUID DELIVERY SYSTEM

CROSS-REFERENCE TO RELATED APPLICATIONS

This application is the national stage application of corresponding international application number PCT/EP2020/075268, filed Sep. 10, 2020, which claims priority to and the benefit of European application no. 19219192.2, filed Dec. 23, 2019, which is hereby incorporated by reference in its entirety.

TECHNICAL FIELD

The present disclosure relates to the field of fluid delivery. More specifically, the present disclosure relates to a fluid delivery system which allows delivery of at least one fluid under predetermined and desired operating conditions. Even more specifically, the present disclosure relates to an injection system for injecting at least one medical fluid.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Delivery systems for administering a liquid composition by injection or by infusion are known in the art.

In the medical field, for instance, a liquid medicament or a diagnostically active contrast agent is injected or infused into a patient's body, generally into a patient's blood vessel that reaches a body portion or a patient's body organ to be treated and/or analyzed (e.g. during scan examinations like X-ray, CT, MRI or ultrasound exams). In some specific applications, the liquid composition to be injected may comprise a suspension of microparticles homogeneously distributed in a liquid carrier, the homogeneity of which is requested to be preserved throughout the delivery thereof. Typically, the liquid composition comprises an aqueous suspension of gas filled microvesicles, namely microbubbles bounded by a surfactant stabilized gas/liquid interface, or microballoons bounded by a tangible material envelope.

Power injectors and mechanically assisted infusion systems for controllably dispensing therapeutically active medications or diagnostically active substances are well known in the art. Typically, such devices include an automatic injector with syringes containing an injectable liquid and a piston movable within the barrel of the syringe to expel said liquid through a tip thereof and then injecting it into a patient via a tubing connected to the syringe tip and to an injecting needle or catheter. For controlling the injections parameters, the piston is driven by means of an electromechanical arrangement that pushes the piston at a desired rate, continuously or at chosen intervals, so that the amount of medication is delivered to the patient's body under strictly determined conditions. For instance, in case of intravenous dispensing contrast agent formulations for diagnostic purposes (during X-ray, CT, MRI or ultrasound exams), the rate and the mode of injection can be accurately controlled to match the requirements of the imaging methods and detector systems used for investigating the circulation or a specific organ in the body.

It is important for the power injectors to control the homogeneity of the liquid composition stored within the syringe barrel during its administration, and this aspect becomes even more important when the injectable formulation is a suspension or dispersion of active particles which tend to settle, coalesce or segregate with time in the syringe. Indeed, even some modest separation of the particles by gravity or otherwise from the carrier liquid in the course of administration of the formulation may have very important influence on reproducibility and reliability of the injection results.

EP 1,035,882B1 and WO 2017/114706 disclose methods and means for keeping the syringe content homogeneous during injection. In details, these documents disclose methods of administering to patients by injection or by infusion a suspension of microparticles homogeneously distributed in a liquid carrier by means of an injector system comprising a syringe containing said suspension and a power-driven piston for injecting said suspension into a patient. According to these methods, the suspension contained in the syringe is subjected to a rotation or rocking motion, thereby maintaining the suspension homogeneous by preventing segregation of the microparticles by gravity or buoyancy, and without damaging said particles or disturbing their distribution.

WO 2016/033351 discloses an infusion system which comprises a double action infusion pump. The pump includes a cylinder and a reciprocating piston received within the cylinder, the reciprocating piston separating a first pump chamber from a second pump chamber of the cylinder. A reciprocating motor is coupled with the reciprocating piston, and the first and second pump chambers alternate between filling and evacuating conditions with reciprocation of the reciprocating piston through operation of the reciprocating motor, and the speed of reciprocation is varied to provide a continuous output of fluid between the first and second pump chambers. A fluid source and a catheter are optionally coupled with the double action infusion pump. The catheter includes one or more infusion ports near a catheter distal portion, and the one or more infusion ports receive and expel the continuous output of fluid from the double action infusion pump.

DE 10 2011 120 105 discloses a device having a container with an opening, in which a movable piston is arranged. A piston rod is provided to displace the piston in the container. The container is divided into chambers. A flexible sealing element is provided to close the opening of the container. Two inlet ducts are communicated with a media feed line and the chambers respectively. Two outlet ducts are communicated with the media feed line and the chambers respectively.

Technical fields different from medical applications may as well require delivery of compositions under specific and predetermined conditions.

For instance, a glue formulation may require to be delivered only when suitable operating conditions are guaranteed, e.g. when a given homogeneity of the glue formulation components is achieved. Therefore, a dedicated delivery system for applying the glue formulation in a given environment should ensure that the glue formulation is actually delivered only when said desired homogeneity is obtained, so that efficient and correct functioning of the glue is guaranteed.

Ensuring a desired homogeneity is required, for instance, also in the processes of preparation of a painting composition or of a coating composition that are carried out immediately before application thereof, e.g. in the automotive, aerospace, housing fixtures industries.

According to further possible applications, a delivery system may be required to start delivering a given composition only when a specific property threshold thereof is achieved, for instance when a predetermined temperature value has been reached. Therefore, the delivery system should ensure that said temperature value is effectively obtained and, moreover, that a proper (typically slow) heat distribution has occurred within said composition.

The aspects mentioned above are applicable not only to traditional industries (like pharma, chemical, automotive, aerospace industries) where a mixing or shaking step is requested to be performed before a final delivery/application step is executed. Indeed, also cellular/biological applications may require that predetermined conditions are maintained or achieved before moving to a successive step. For instance, many experiments involving cells cultures make use of bovine serum which is typically required to be regularly mixed by careful swirling before use in order to keep its native structural state.

The Applicant has thus perceived the need of improving the capability of a fluid delivery system to deliver a fluid which satisfies specific and predetermined fluid properties that are requested for a proper use of that fluid.

In other words, the Applicant has perceived the need of providing a fluid delivery system which can satisfy and guarantee the required delivery conditions for the specific fluid to be delivered, meanwhile ensuring that the delivery system is accurate, efficient, reliable and simple as far as easiness of use and manufacturing process thereof are concerned.

Moreover, the Applicant has perceived the need of providing a fluid delivery system which allows, if needed, to reach sufficiently high fluid pressures and to deliver the fluid at sufficiently high flow rates while avoiding, or at least significantly limiting, the necessity of setting up complex structural solutions of the delivery system for guaranteeing that said sufficiently high fluid pressures and flow rates can be finally achieved.

SUMMARY

A simplified summary of the present disclosure is herein presented to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In order to ensure that predefined delivery requirements of a given fluid are achieved before the fluid is started to be delivered, the Applicant has found that a proper recirculation of the fluid within the fluid delivery system allows to guarantee the desired efficiency and quality thereof.

Moreover, the Applicant has found that suitably re-directing the fluid within the fluid delivery system before being delivered outside thereof provides for a pressure equalization within the fluid delivery system which advantageously contributes in easily managing the fluid circulation and also in reducing the technical constraints which are inevitably faced when high pressures are generated.

Furthermore, the Applicant has found that recirculation of the fluid within the fluid delivery system before being delivered outside thereof advantageously allows to remarkably reduce or even completely remove the risk of pressure pulsations, especially at the beginning of the fluid delivery procedure.

The Applicant has also found that recirculation of the fluid within the fluid delivery system before being delivered outside thereof advantageously allows to remarkably reduce or even completely eliminate the latency time of the fluid delivery system, as it will be described in more detail in the following of the present description.

Therefore, an aspect of the present disclosure provides for a fluid delivery system comprising:
  at least one supply station for supplying a fluid;
  a pressurizing unit for pressurizing the fluid comprising:
    a pump module comprising a chamber and a piston contained therein, said piston having a plunger that, in cooperation with internal walls of said chamber, defines first and second variable-volume sub-chambers, and
    a driving unit connected to said piston for reciprocating the piston within said chamber;
  an inlet fluid circuit in fluid communication with said at least one supply station and with said pump module for supplying the fluid to said first and second variable-volume sub-chambers;
  an outlet fluid circuit in fluid communication with said pump module for discharging the fluid alternatively from said first and second variable-volume sub-chambers, said outlet fluid circuit being separate from said inlet fluid circuit;
  a recirculation fluid circuit fluidically connecting said first and second variable-volume sub-chambers, and
  an actuator for managing the fluid passage in both directions between said first and second variable-volume sub-chambers, said actuator being part of said recirculation fluid circuit.

A further aspect of the present disclosure provides for a method of operating a fluid delivery system comprising a pressurizing unit provided with a pump module that comprises a chamber and a piston reciprocating therein, said piston having a plunger which, in cooperation with inner walls of said chamber, defines first and second variable-volume sub-chambers, the fluid delivery system further comprising a recirculation fluid circuit and an actuator associated thereto for fluidically connecting said first and second variable-volume sub-chambers, said method comprising the step of operating said actuator for regulating a passage of fluid between said first and second variable-volume sub-chambers in both directions in order to balance the fluid pressure within said first and second variable-volume sub-chambers when delivery of the fluid outside of the fluid delivery system is not performed.

A further aspect of the present disclosure provides for a method of operating a fluid delivery system comprising a pressurizing unit provided with a pump module that comprises a chamber and a piston reciprocating therein, said piston having a plunger which, in cooperation with inner walls of said chamber, defines first and second variable-volume sub-chambers, the fluid delivery system further comprising a recirculation fluid circuit and an actuator associated thereto for fluidically connecting said first and second variable-volume sub-chambers, said method comprising the steps of:
  supplying a fluid from at least one supply station (10) to said first and second variable-volume sub-chambers;
  axially translating the piston within said chamber;
  operating the actuator to circulate the fluid from said first variable-volume sub-chamber to said second variable-volume sub-chamber through said recirculation fluid circuit, and vice versa, during multiple axial translations of the piston within the chamber, and closing the actuator and delivering the fluid out of the fluid delivery system.

More specifically, one or more aspects of the present disclosure are set out in the independent claims, and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solutions of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
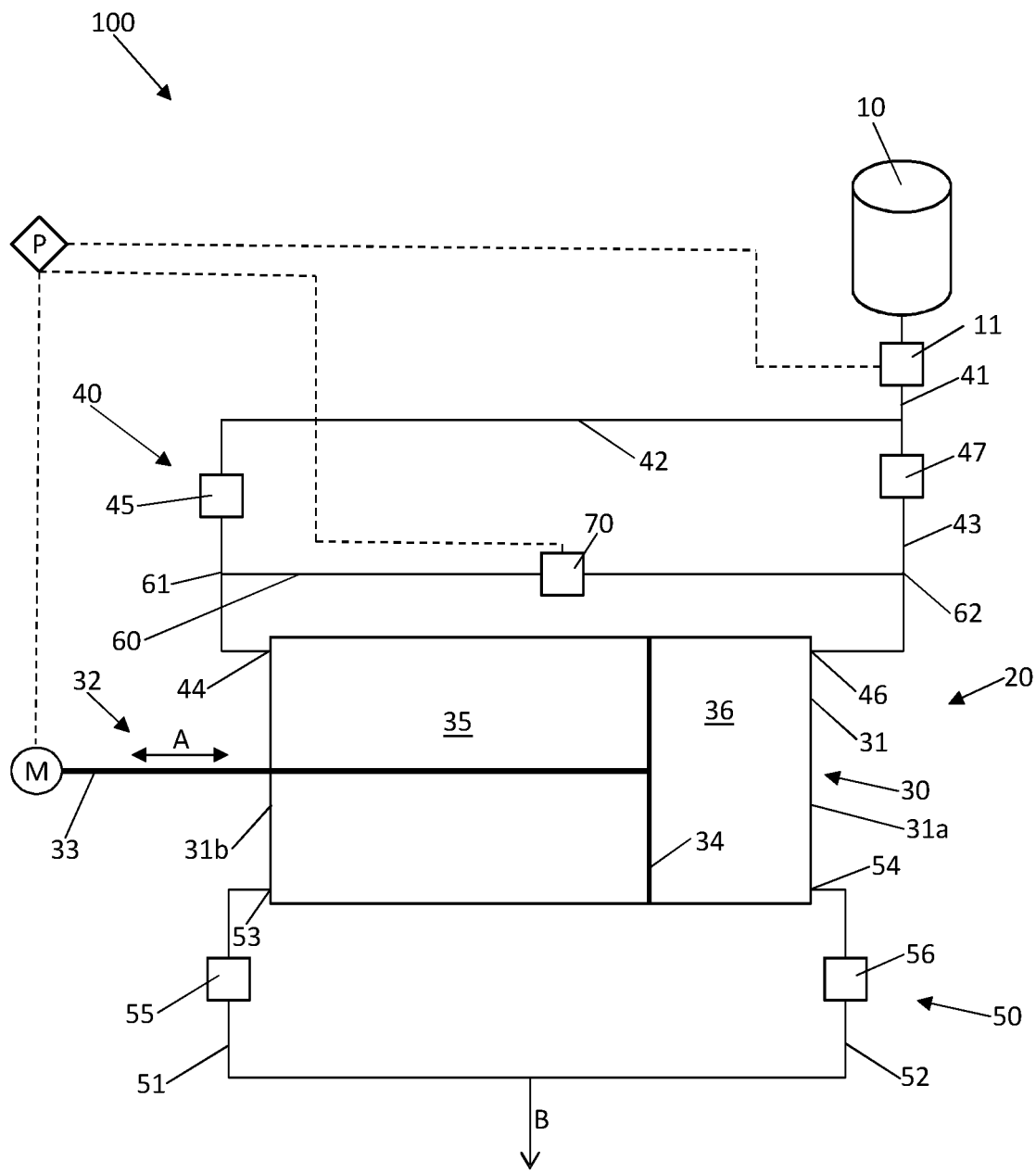
FIG. 1 shows a schematic representation of a fluid delivery system according to an embodiment of the present disclosure.

With reference to FIG. 1, a schematic representation of a fluid delivery system 100 is shown according to an embodiment of the present disclosure. Fluid delivery system 100 is used for delivering a fluid contained in a supply station 10, said fluid being of different nature on the basis of the specific technical field wherein the fluid delivery system is implemented.

For instance, in case fluid delivery system 100 is an injection system for being used in the medical field, the fluid contained in supply station 10 and to be injected into the patient's vascular system can be a contrast agent which is administered for enhancing contrast of target (body) features (for example, human body's structures or organs) within the patients during scan examinations thereof, e.g. during CT, MRI or ultrasound exams. Particularly, in imaging applications (wherein a visual representation of the interior of the patients is created in a non-invasive way without turning to surgery techniques) the use of a contrast agent makes the target features more conspicuous. As a result, target features that would otherwise be less distinguishable from other nearby features (for example, surrounding tissues) are advantageously highlighted. This significantly facilitates the task of clinicians in diagnostic applications, and particularly the identification and/or characterization of lesions, the monitoring of their evolution or response to medical treatments. For example, in CT applications the contrast agent may be an iodine-based contrast agent comprising diatrizoate, ioxaglate, iopamidol, iohexol, ioxilan, iopromide or iodixanol. An example of a commercial contrast agent comprising iopamidol is ISOVUE®, manufactured by Bracco Diagnostics Inc. °.

According to an embodiment of the present disclosure, fluid delivery system 100 is configured for delivering Ultrasound Contrast Agents (USCA) in a continuous injection/infusion mode and/or as a bolus. In particular, fluid delivery system 100 is used for delivering a liquid composition which comprises a suspension of microparticles homogeneously distributed in a liquid carrier, preferably an aqueous liquid carrier, said microparticles containing entrapped pure gases or gas mixtures including at least one physiologically acceptable halogenated gas. This halogenated gas is preferably selected among CF4, C2F6, C3F8, C4F8, C4F10, C5F12, C6F14 or SF6. The gas mixtures can also contain gases such as air, oxygen, nitrogen, helium, xenon or carbon dioxide. In a number of cases said microparticles (microbubbles or microballoons) contain mixtures of nitrogen or air with at least one perfluorinated gas in proportions which may vary between 1 and 99%. An example of a commercial contrast agent that is used in Contrast Enhanced Ultrasound (CEUS) applications is SonoVue® (Sulphur hexafluoride microbubbles), manufactured by Bracco Suisse®.

Still referring to the medical field, the fluid contained in supply station 10 and to be injected into the patient's vascular system can also be a saline solution comprising a physiological or isotonic solution (e.g. sodium chloride). Alternatively, said fluid can be a liquid medicament or a drug.

As already mentioned above, delivery system 100 of the present disclosure can be used for delivering fluids in many technological fields, not necessarily correlated to the medical/diagnostic field. For instance, the fluid contained in supply station 10 can be a glue formulation, a painting formulation, a coating formulation, or a substance/formulation for which a delivery property (e.g. temperature) is requested to be properly reached/controlled.

Fluid delivery system 100 comprises a pressurizing unit 20 which operates on the fluid so that it will exit the fluid delivery system (and thus it will be delivered) at a predetermined pressure and flow rate, previously set up based on the requirements correlated to the specific delivery use. In detail, pressurizing unit 20 comprises a pump module 30 and a driving unit M, said driving unit being associated to the pump module for the operation thereof. Pump module 30 comprises a chamber 31 within which a piston 32 is reciprocated (i.e. moved back and forth—see double arrow A) by driving unit M. According to the embodiment shown in the figures, chamber 31 is represented as a cylindrical barrel (e.g. like a syringe barrel); however, other different configurations suitable for the purpose can be envisaged as well. Piston 32 comprises a piston rod 33 and a plunger 34, the plunger being arranged to be substantially perpendicular to the piston rod and having a radial extension which substantially corresponds to the chamber radial extension, i.e. to the chamber width. Therefore, in cooperation with internal walls of chamber 31, plunger 34 defines a first sub-chamber 35 on one side of the plunger (on the left side of the plunger in the embodiment of FIG. 1) and a second sub-chamber 36 on the opposite side of the plunger (on the right side of the plunger in the embodiment of FIG. 1). During operation of the fluid delivery system, piston 32 is moved back and forth (see double arrow A) and thus the overall volume of said first and second sub-chambers 35, 36 is continuously and alternately changing, thus these sub-chambers being variable-volume sub-chambers. For instance, when piston 32 is moved to the right in FIG. 1, the volume of first sub-chamber 35 is increased while the volume of second sub-chamber 36 is decreased; on the contrary, when piston 32 is moved to the left in FIG. 1, the volume of second sub-chamber 36 is increased while the volume of first sub-chamber 35 is decreased. According to the embodiment shown in FIG. 1, plunger 34 is provided at an axial end of piston rod 33 (i.e. at the axial end opposite to the axial end connected to driving unit M). Alternatively, plunger 34 can be provided at a different position along the longitudinal extension of piston rod 33 (embodiment not shown in the figures) with the proviso that both base walls 31*a*,31*b* of chamber 31 allow a sealed axial movement of piston rod 33 therethrough.

Fluid delivery system 100 of the present disclosure further comprises an inlet fluid circuit 40 which is in fluid communication with supply station 10 and with pump module 30. Inlet fluid circuit 40 comprises fluid pathways which supply the fluid (contained in supply station 10) to first variable-volume sub-chamber 35 and to second variable-volume sub-chamber 36 so that chamber 31 is filled with a suitable fluid volume amount to be delivered (arrow B).

In detail, inlet fluid circuit 40 comprises a first inlet fluid pathway 41 which is in fluid communication with supply station 10, said first inlet fluid pathway 41 including a supply station valve 11 that allows the fluid to be discharged from supply station 10. Supply station valve 11 is an active valve that is operated by the fluid delivery system, as it will be explained in detail in the following of the present description.

Downstream from supply station valve 11, inlet fluid circuit 40 branches into a second inlet fluid pathway 42 and a third inlet fluid pathway 43 which are in fluid communication with first sub-chamber 35 and second sub-chamber 36, respectively. First sub-chamber 35 is provided with a first inlet port 44 which allows second inlet fluid pathway 42 to be in fluid communication with first sub-chamber 35. Analogously, second sub-chamber 36 is provided with a second inlet port 46 which allows third inlet fluid pathway 43 to be in fluid communication with second sub-chamber 36.

Upstream from the first inlet port 44, second inlet fluid pathway 42 is provided with a first inlet fluid circuit valve 45 which allows the fluid to flowing into first sub-chamber 35 through second inlet fluid pathway 42. According to an embodiment of the present disclosure, first inlet fluid circuit valve 45 is a check valve, i.e. a one-way valve which allows the fluid to flow through it in only one direction, specifically from supply station 10 towards first sub-chamber 35, thereby avoiding that the fluid flows back towards supply station 10.

Analogously, upstream from second inlet port 46, third inlet fluid pathway 43 is provided with a second inlet fluid circuit valve 47 which allows the fluid to flowing into second sub-chamber 36 through third inlet fluid pathway 43. According to an embodiment of the present disclosure, second inlet fluid circuit valve 47 is a check valve, i.e. a one-way valve which prevents reverse flow allowing the fluid to flow through it in only one direction, specifically from supply station 10 towards second sub-chamber 36, thereby avoiding that the fluid flows back towards supply station 10.

Preferably, first and second inlet fluid circuit valves 45, 47 are ball check valves wherein a ball is present inside the body valve for regulating the fluid flow.

Fluid delivery system 100 further comprises an outlet fluid circuit 50 which is separate from inlet fluid circuit 40. Outlet fluid circuit 50 is in fluid communication with pump module 30 and it comprises a first outlet fluid pathway 51 and a second outlet fluid pathway 52 that allow fluid delivery system 100 to discharge the fluid from chamber 31 and to deliver it outside the fluid delivery system (see arrow B). In detail, first sub-chamber 35 is provided with a first outlet port 53 which allows first outlet fluid pathway 51 to be in fluid communication with first sub-chamber 35. Analogously, second sub-chamber 36 is provided with a second outlet port 54 which allows second outlet fluid pathway 52 to be in fluid communication with second sub-chamber 36. As it will be described in detail in the following of the present disclosure, in operation first and second outlet fluid pathways 51, 52 of outlet fluid circuit 50 discharge the fluid alternatively from first sub-chamber 35 and from second sub-chamber 36.

Downstream from first outlet port 53, first outlet fluid pathway 51 is provided with a first outlet fluid circuit valve 55 which allows the fluid to being discharged from first sub-chamber 35 through first outlet fluid pathway 51. According to an embodiment of the present disclosure, first outlet fluid circuit valve 55 is a check valve, i.e. a one-way valve which prevents reverse flow allowing the fluid to flow through it in only one direction, specifically exiting from first sub-chamber 35, thereby avoiding that the fluid flows back into said first sub-chamber 35.

Analogously, downstream from second outlet port 54, second outlet fluid pathway 52 is provided with a second outlet fluid circuit valve 56 which allows the fluid to being discharged from second sub-chamber 36 through second outlet fluid pathway 52. According to an embodiment of the present disclosure, second outlet fluid circuit valve 56 is a check valve, i.e. a one-way valve which allows the fluid to flow through it in only one direction, specifically exiting from second sub-chamber 36, thereby avoiding that the fluid flows back into said second sub-chamber 36.

Preferably, first and second outlet fluid circuit valves 55, 56 are spring loaded check valves wherein a spring component is used to support valve operation by eliminating the effect of gravity on the check valve function. More preferably, first and second outlet fluid circuit valves 55, 56 are spring loaded ball check valves.

According to the present disclosure, fluid delivery system 100 further comprises a recirculation fluid circuit 60 fluidically connecting said first and second variable-volume sub-chambers 35, 36, said recirculation fluid circuit 60 cooperating with an actuator 70 for managing the fluid passage in both directions between said first and second variable-volume sub-chambers 35, 36. Recirculation fluid circuit 60 is an additional fluid circuit, i.e. a further fluid pathway which allows a direct fluid communication between first and second variable-volume sub-chambers 35, 36. Therefore, in the present description the terms recirculation fluid circuit or additional fluid circuit or recirculation fluid pathway are equivalent to each other and meant to indicate the same component of the fluid delivery system.

According to the embodiment shown in FIG. 1, recirculation fluid circuit 60 is external to chamber 31 and it fluidically connects separate branches of inlet fluid circuit 40 upstream from the inlet ports of sub-chambers 35, 36 and downstream from inlet fluid circuit valves 45, 47. In detail, a first axial end 61 of recirculation fluid circuit pathway 60 fluidically connects with second inlet fluid pathway 42 of inlet fluid circuit 40 downstream from first inlet fluid circuit valve 45. Analogously, a second axial end 62 of recirculation fluid circuit 60 fluidically connects with third inlet fluid pathway 43 of inlet fluid circuit 40 downstream from second inlet fluid circuit valve 47.

Actuator 70 is an active valve that is operated by the fluid delivery system, as it will be explained in detail in the following of the present description. Preferably, actuator 70 is an electro-mechanical driven valve that is automatically controlled and operated by a processor P of fluid delivery system 100. As schematically shown in the figures, processor P controls and operates actuator 70, driving unit M and supply station valve 11. In other words, processor P is a control unit which governs and actuates some components of the fluid delivery system in accordance with a predetermined delivery (injection) protocol selected by the operator.

Figure 2:
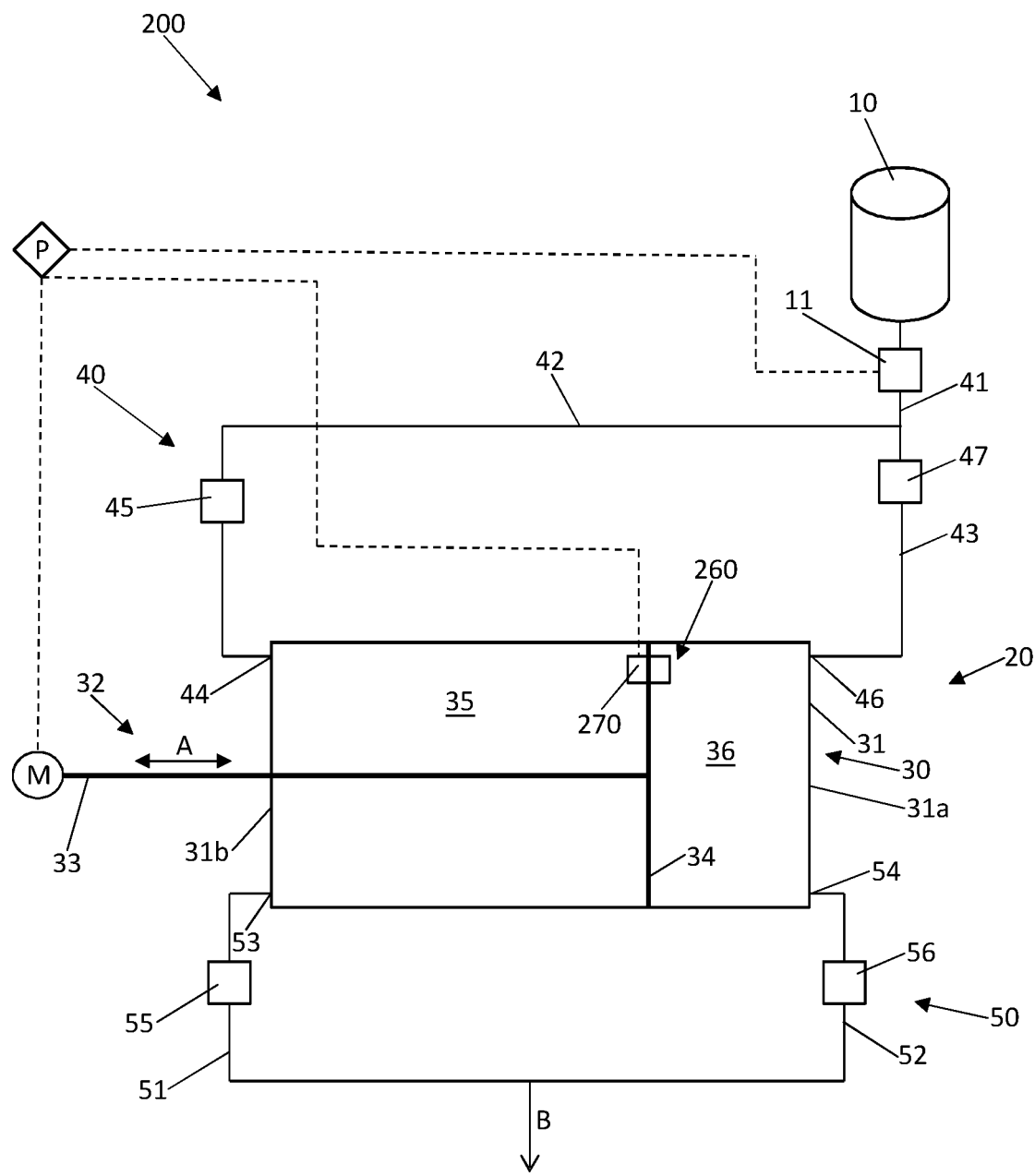
FIG. 2 shows a schematic representation of an alternative fluid delivery system according to a further embodiment of the present disclosure.

According to an alternative embodiment shown in FIG. 2, a fluid delivery system 200 comprises a recirculation fluid circuit 260 and an actuator 270 which are positioned inside chamber 31. In particular, both recirculation fluid circuit 260 and actuator 270 are integral with plunger 34 of piston 32, i.e. integrated within the plunger component. In detail, recirculation fluid circuit 260 comprises a fluid passage obtained within the plunger thickness for ensuring fluid communication between sub-chambers 35, 36. In other words, recirculation fluid circuit 260 is a duct (through hole) provided in the plunger, the diameter (radial extension) of said duct being remarkably lower than the plunger extension (length).

According to said alternative embodiment shown in FIG. 2, actuator 270 is arranged inside recirculation fluid circuit 260 and it is automatically controlled and operated by processor P of fluid delivery system 200.

Figure 3:
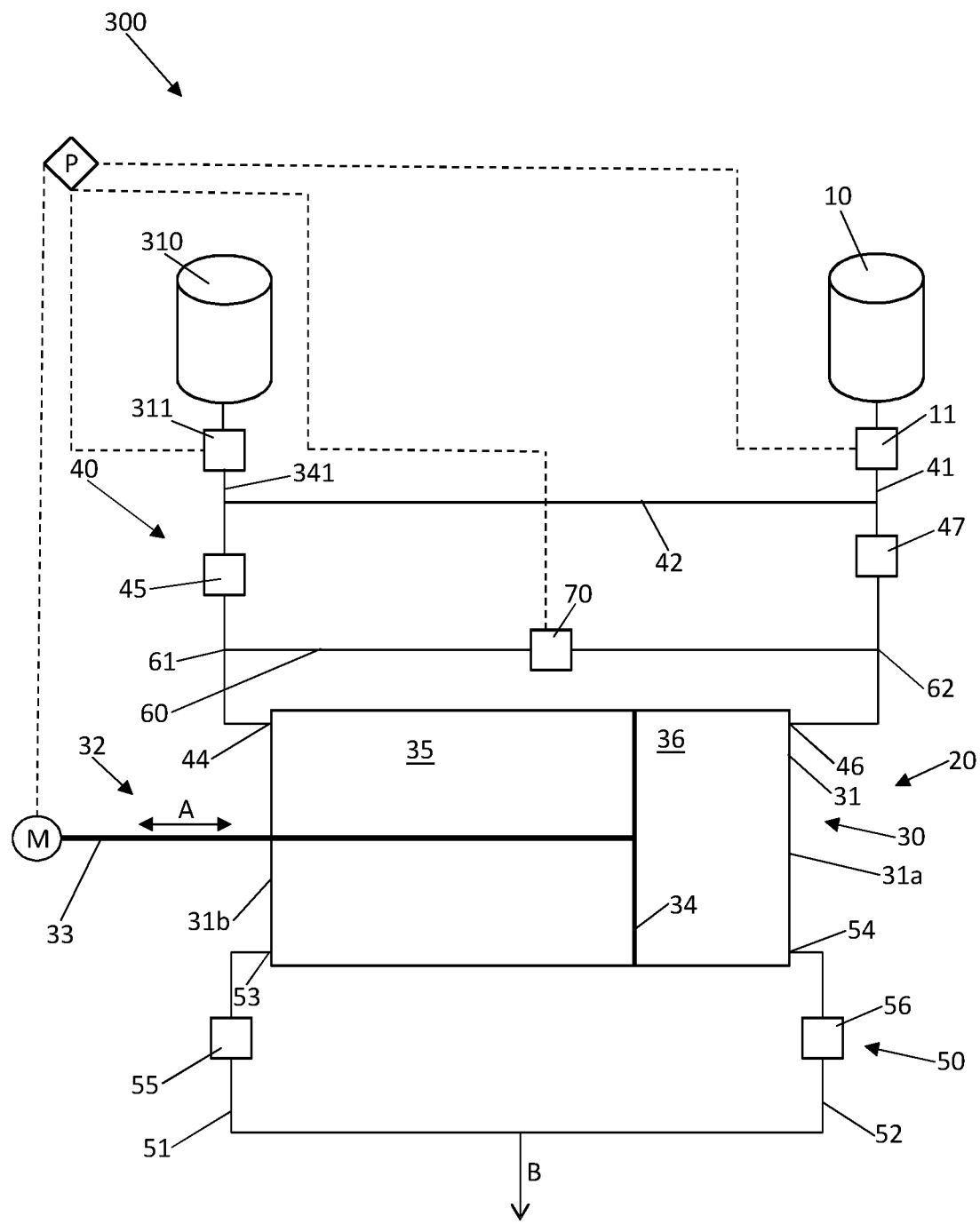
FIG. 3 shows a schematic representation of an alternative fluid delivery system according to a further embodiment of the present disclosure.

According to an alternative embodiment shown in FIG. 3, fluid delivery system 300 comprises an additional supply station 310 containing the same fluid stored in supply station 10. Analogously to the embodiment shown in FIG. 1, inlet fluid circuit 40 comprises an additional first inlet fluid pathway 341 which fluidically connects additional supply station 310 to second inlet fluid pathway 42 of inlet fluid circuit 40. Moreover, said additional first inlet fluid pathway 341 comprises an additional supply station valve 311 that allows the fluid to be discharged from additional supply station 310. Additional supply station valve 311 is an active valve that is operated by the fluid delivery system, as it will be explained in detail in the following of the present description. The additional supply station is envisaged either to provide the fluid delivery system with a back-up solution in case of malfunction of the first supply station, or to provide a fluid supplemental source for increasing autonomy of the fluid delivery system as well as for ensuring fluid delivery continuity when the first supply station 10 is running out of fluid.

Figure 4:
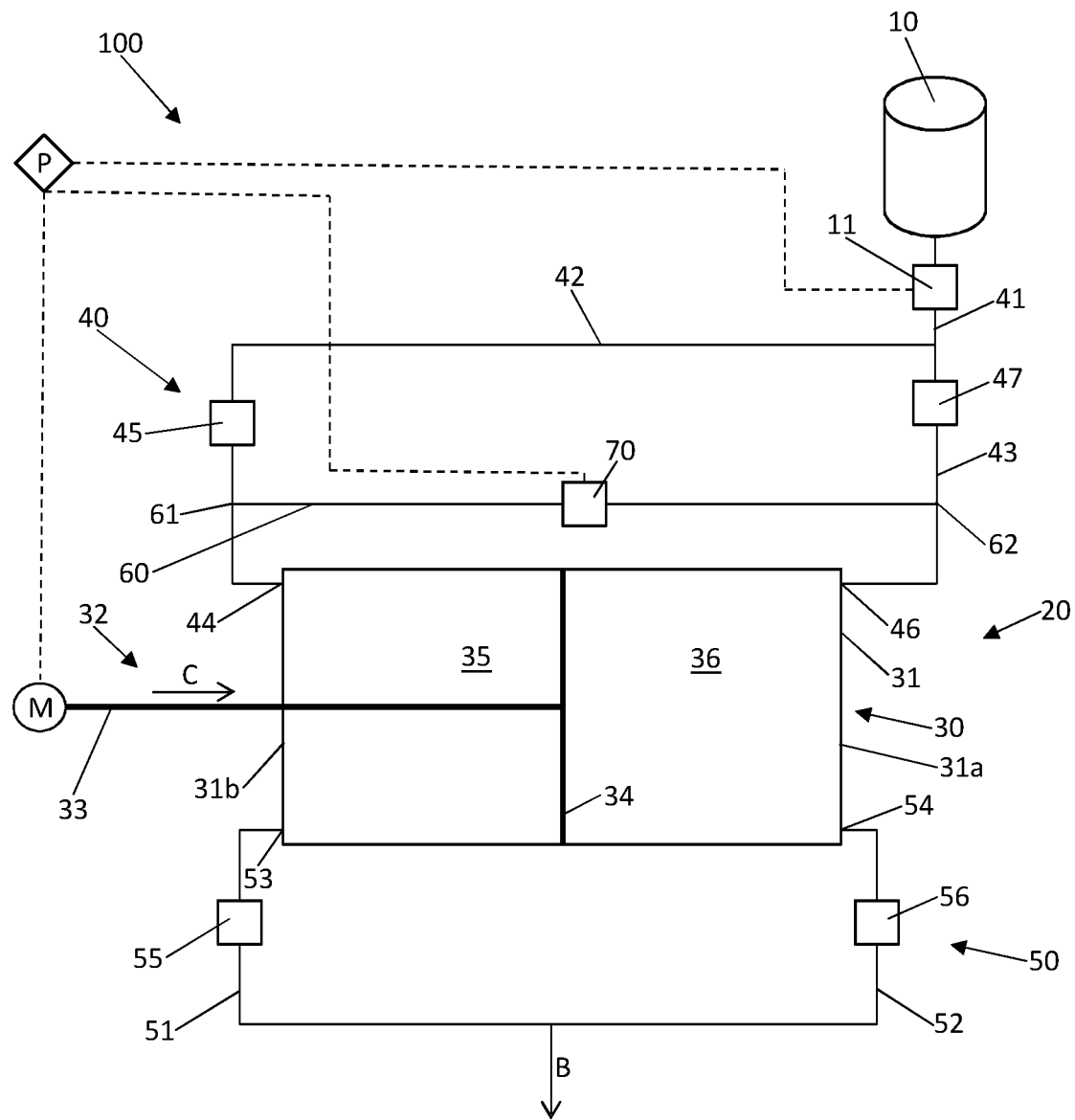
FIG. 4 to FIG. 6 show a schematic representation of the operation steps of the fluid delivery system shown in FIG. 1, and FIG. 7 and FIG. 8 show a schematic representation of the operation steps of the fluid delivery system shown in FIG. 2.

Operation of the delivery system according to the first embodiment (shown in FIG. 1) of the present disclosure is described in the following with reference to FIG. 4-FIG. 6.

Supply station 10 contains the fluid (not shown) which has to be delivered by delivery system 100 (arrow B).

As a first initiation step, the method of delivery according to the present disclosure comprises the step of filling first and second sub-chambers 35, 36 with the fluid to be delivered. In order to perform said filling step, processor P opens supply station valve 11, closes actuator 70 of recirculation fluid circuit 60 and acts on driving unit M for moving piston 32 within chamber 31, thereby allowing the fluid to exit supply station 10 and to flow through inlet fluid circuit 40.

In detail, as soon as piston 32 is axially translated along a first direction (e.g. arrow C of FIG. 4), under pressure is generated in the first sub-chamber (e.g. sub-chamber 35) which is increasing its volume due to the piston axial movement, and the fluid flows through first inlet fluid pathway 41 and through second inlet fluid pathway 42 of inlet fluid circuit 40, through the corresponding first inlet fluid circuit valve (e.g. first inlet fluid circuit valve 45), and then it enters and fills said first sub-chamber. At the same time, the air contained within the second sub-chamber (e.g. sub-chamber 36)—which is decreasing its volume due to the piston axial movement—is primed away from the delivery system through venting means possessed by the opposite second inlet fluid circuit valve (e.g. second inlet fluid circuit valve 47). Successively, in order to fill the second sub-chamber and prime the first sub-chamber, processor P acts on driving unit M for inverting the piston movement so that the piston is axially translated along a second direction opposite to the first direction (e.g. arrow D of FIG. 5). Since actuator 70 is kept closed while the piston is moving, under pressure is generated in the second sub-chamber (e.g. sub-chamber 36) which is increasing its volume due to the piston axial movement, and the fluid flows through first inlet fluid pathway 41 of inlet fluid circuit 40, through the corresponding second inlet fluid circuit valve (e.g. second inlet fluid circuit valve 47), and then it enters and fills said second sub-chamber. At the same time, the air still contained within the first sub-chamber (e.g. sub-chamber 35)—which is decreasing its volume due to the piston axial movement—is primed away from the delivery system through venting means possessed by the corresponding first inlet fluid circuit valve (e.g. first inlet fluid circuit valve 45). During the priming step some fluid exits the delivery system so that priming of the outlet fluid circuit 50 is performed too.

Alternatively, air priming of the fluid delivery system is performed by dedicated venting means (not shown in the drawings) which is separate from the fluid circuit valves. According to an embodiment, a dedicated venting means is associated with each valve of the fluid delivery system. According to a further embodiment, only one dedicated venting means is possessed by the fluid delivery system. Preferably said only one dedicated venting means is associated to the actuator of the recirculation fluid circuit.

As soon as chamber 31 is filled up with the fluid and priming of the delivery system is completed, processor P closes supply station valve 11 and opens actuator 70 of recirculation fluid circuit 60, while driving unit M is still activated and keeps piston 32 axially translating within chamber 31.

Alternatively, processor P opens actuator 70 of recirculation fluid circuit 60 while still keeping supply station valve 11 open.

While piston 32 is moving towards base wall 31a of chamber 31 (see arrow C of FIG. 4), translation of plunger 34 causes a volume increase of first sub-chamber 35 and a corresponding volume decrease of second sub-chamber 36. Moreover, since actuator 70 is in an open state at this stage of the procedure, the fluid initially contained within second sub-chamber 36 is pushed by plunger 34 out of chamber 31 passing through second inlet port 46 and then, by flowing into recirculation fluid circuit 60 and, by passing through open actuator 70, it enters first sub-chamber 35 by accessing first inlet port 44.

It has to be pointed out that the fluid contained inside second sub-chamber 36 and pushed by plunger 34 is allowed neither flowing back into supply station 10 nor accessing second outlet fluid pathway 52 of outlet fluid circuit 50. In fact, supply station valve 11 is closed and both first and second inlet fluid circuit valves 45, 47 are one-way valves which allow the fluid flowing from supply station 10 into chamber 31, but not vice versa, thereby avoiding the fluid discharged from sub-chamber 36 flowing back through first and second inlet fluid pathways 41, 42 of inlet fluid circuit 40. Moreover, since second outlet fluid circuit valve 56 automatically opens only when the fluid discharged from second sub-chamber 36 has a sufficiently high pressure for overcoming the internal resilience of said valve (preferably, second outlet fluid circuit valve 56 is a ball spring-loaded check valve), when actuator 70 is in the open state the fluid discharged from second sub-chamber 36 does not have enough force to overcome the internal resilience of second outlet fluid circuit valve 56, and thus the fluid is not delivered outside of fluid delivery system 100, on the contrary the fluid discharged from second sub-chamber 36 re-fills first sub-chamber 35.

Figure 5:
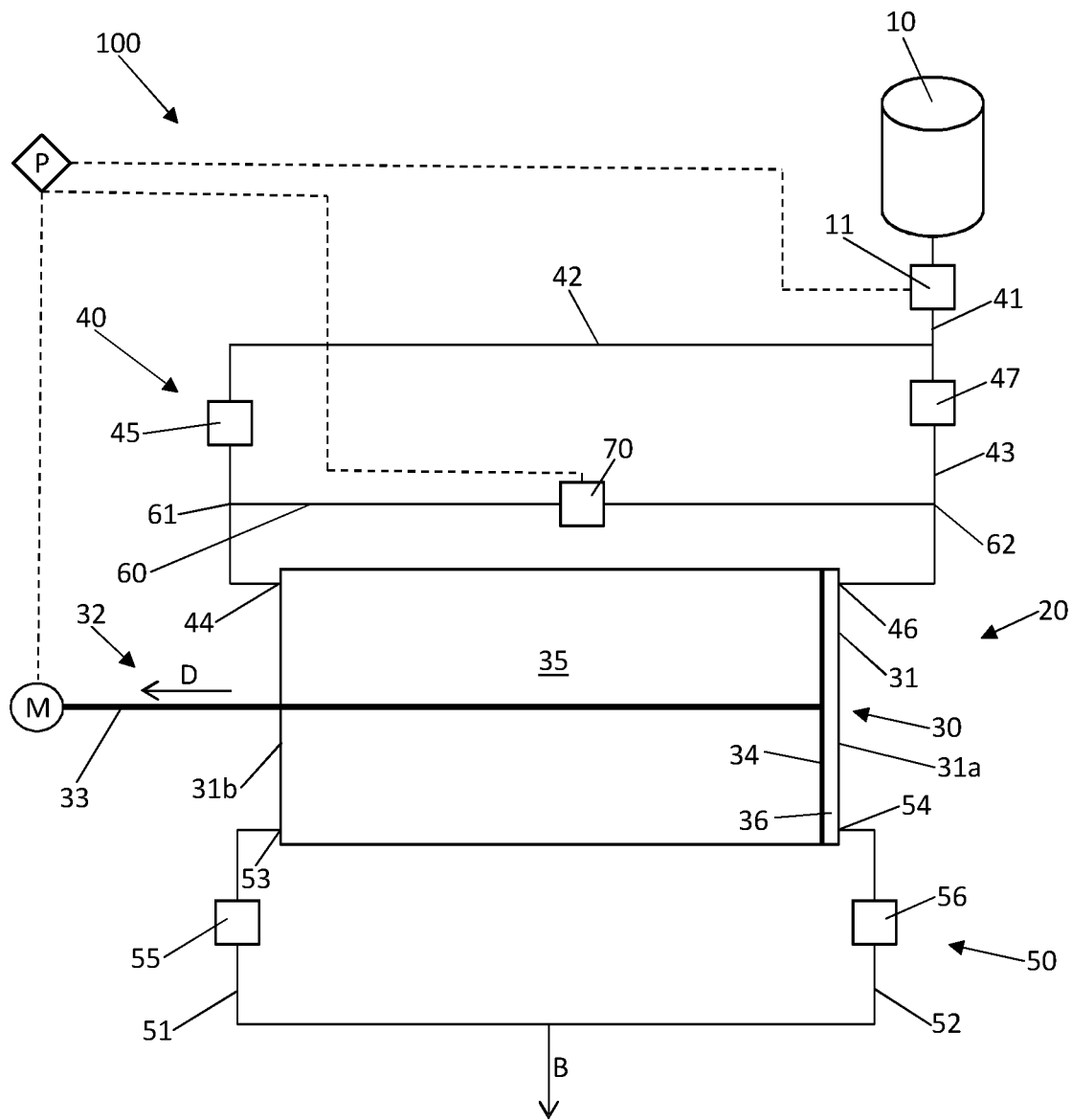
Figure 6:
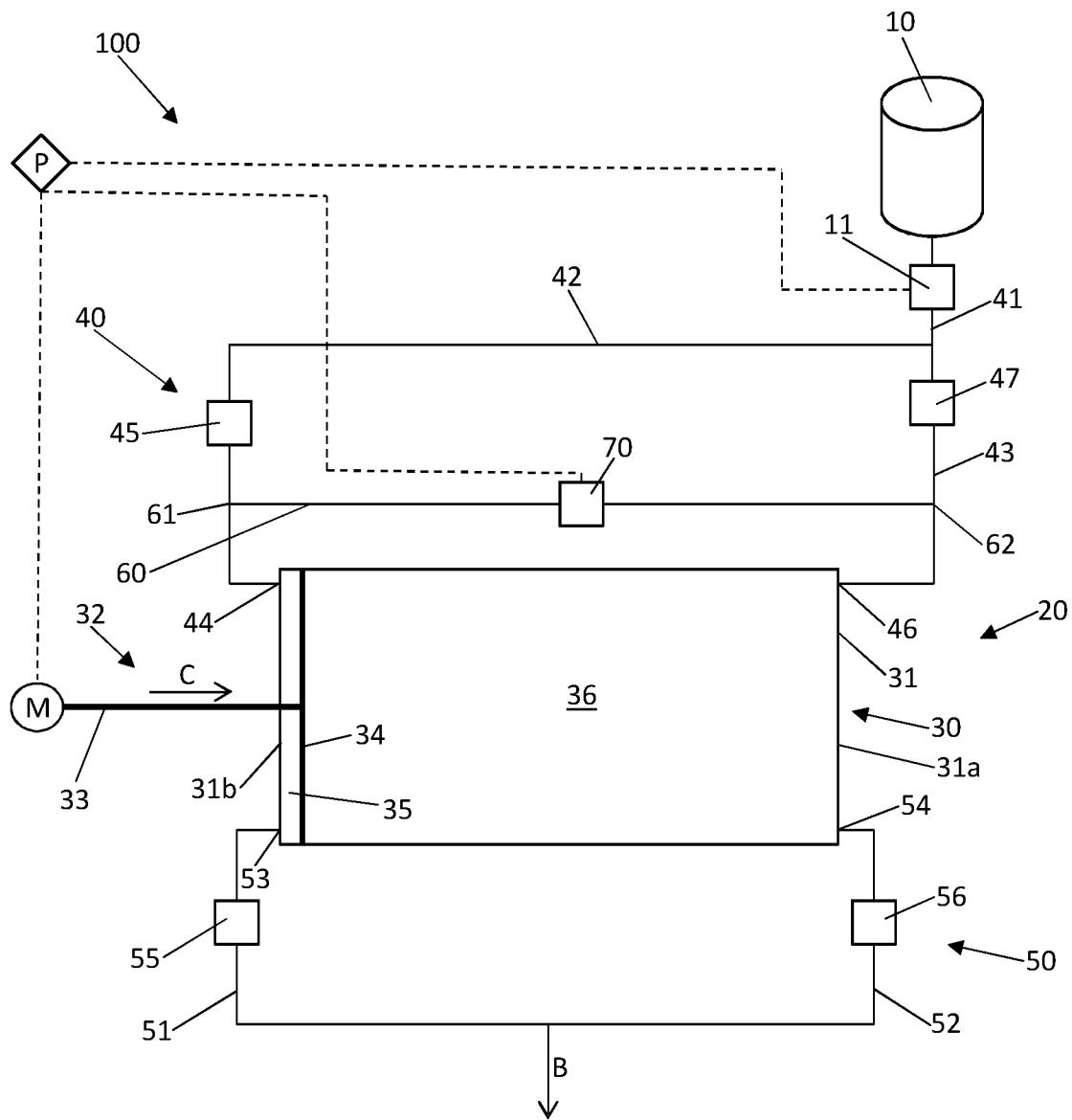

As soon as piston 32 has reached its first end-stop, i.e. plunger 34 has completed its axial translation in a first direction (right direction in FIG. 4—see arrow C) and it arrives in proximity of base wall 31a of chamber 31 so that second sub-chamber 36 contains a substantially small volume of fluid while first sub-chamber 35 contains a large volume of fluid, processor P acts on driving unit M to reverse piston axial translation (left direction in FIG. 5—see arrow D). During reverse movement of piston 32 within chamber 31 the same operative conditions mentioned above still apply, i.e. actuator 70 is kept in its open state while supply station valve 11 is kept in its closed state.

Axial translation of the plunger in the reverse direction causes a volume increase of second sub-chamber 36 and a corresponding volume decrease of first sub-chamber 35. Thanks to actuator 70 being in its open state, the fluid initially contained within first sub-chamber 35 is pushed by plunger 34 out of chamber 31 passing through first inlet port 44 and then, flowing into recirculation fluid circuit 60 and through open actuator 70, it enters second sub-chamber 36 passing through second inlet port 46.

The considerations provided above with reference to piston translation in a first direction (right direction of FIG. 4—see arrow C) still apply also to piston translation in a second direction, opposite to first direction (left direction of FIG. 5—see arrow D). Therefore, the fluid contained inside first sub-chamber 35 and pushed by plunger 34 is allowed neither flowing back into supply station 10 nor accessing first outlet fluid pathway 51 of outlet fluid circuit 50. In fact, supply station valve 11 is closed and both first and second inlet fluid circuit valves 45, 47 are one-way valves which allow the fluid flowing from supply station 10 into chamber 31, but not vice versa, thereby avoiding the fluid discharged from first sub-chamber 35 flowing back through first and second inlet fluid pathways 41, 42 of inlet fluid circuit 40. Moreover, since first outlet fluid circuit valve 55 automatically opens only when the fluid discharged from first sub-chamber 35 has a sufficiently high pressure for overcoming the internal resilience of said valve (preferably, first outlet fluid circuit valve 55 is a ball spring-loaded check valve), when actuator 70 is in the open state the fluid discharged from first sub-chamber 35 does not have enough force to overcome the internal resilience of first outlet fluid circuit valve 55, and thus the fluid is not delivered outside of fluid delivery system 100, on the contrary the fluid discharged from first sub-chamber 35 re-fills second sub-chamber 36.

As soon as piston 32 has reached its second end-stop, i.e. plunger 34 has completed its axial translation in the second direction (left direction in FIG. 5—see arrow D) and it arrives in proximity of base wall 31b of chamber 31 so that first sub-chamber 35 contains a substantially small volume of fluid while second sub-chamber 36 contains a large volume of fluid, processor P acts on driving unit M to reverse again piston axial translation (right direction in FIG. 6—see arrow C), thereby starting a new charge/discharge cycle of chamber 31 of fluid delivery system 100. Of course, any number of cycles can be arranged for, said number depending on the requirements of the specific fluid to be delivered and on the requirements of the specific application where the delivery system is implemented.

It is apparent from the above that the fluid delivery system of the present disclosure allows a continuous and predefined movement (e.g. in terms of volumes, piston translational speed) of the fluid before exiting the fluid delivery system. As already mentioned above, this aspect of the present disclosure is particularly advantageous in case a specific fluid property (e.g. composition homogeneity, temperature, viscosity, mixture, fluidity) is requested to be achieved and/or maintained before starting delivery of the fluid. In fact, the fluid delivery system according to the present disclosure allows the fluid introduced into chamber 31 to be continuously recirculated by being alternately charged/discharged between first and second sub-chambers 35, 36 when fluid delivery system 100 is not delivering, i.e. the fluid is not definitely exiting the fluid delivery system. Thanks to recirculation fluid circuit 60 and actuator 70 associated thereto, recirculation of the fluid and redistribution thereof between the two sub-chambers contributes in balancing the pressure therein. This aspect is particularly advantageous since it allows to operate the system at a limited (low) pressure, at least in the initial stage when the delivery system is not yet delivering the fluid outside the system, thereby limiting the technical constraints which would need to be implemented if the system were required to operate at higher pressure values.

Furthermore, the method of delivery according to the present disclosure comprises the step of starting delivery (i.e. outside of the fluid delivery system) of the fluid contained within chamber 31. In order to perform said step, processor P closes actuator 70 of recirculation fluid circuit 60 and it opens supply station valve 11. Therefore, during delivery of the fluid (fluid exiting the delivery system—see arrow B), supply station valve 11 is maintained in its open state because it is important to refill the sub-chambers with new fluid in order to avoid fluidic perturbations possibly impacting on the correct functioning of the piston and, consequently, of the overall delivery system. Since closing actuator 70 prevents any fluid to flow through recirculation fluid circuit 60 (while, as already mentioned above, first and second inlet fluid circuit valves 45, 47 do not allow any flow back of the fluid towards supply station 10), pushing plunger 34 in the first direction (arrow C) and in the second opposite direction (arrow D) allows the fluid to exit, respectively, second outlet port 54 and first outlet port 53. Therefore, when the fluid is pushed to pass through second outlet port 54 (arrow C), the fluid flows into second outlet fluid pathway 52 of outlet fluid circuit 50 and then it passes through second outlet fluid circuit valve 56 because at this stage of the procedure, since actuator 70 is closed, the fluid pressure is sufficiently high to overcome the internal resilience of said second outlet fluid circuit valve 56. Analogously, when the fluid is pushed to pass through first outlet port 53 (arrow D), the fluid flows into first outlet fluid pathway 51 of outlet fluid circuit 50 and then it passes through first outlet fluid circuit valve 55 because at this stage of the procedure, since actuator 70 is closed, the fluid pressure is sufficiently high to overcome the internal resilience of said first outlet fluid circuit valve 55. Consequently, the fluid is finally delivered (arrow B) by sequentially discharging it from first and second sub-chambers 35, 36. In fact, since first and second outlet fluid circuit valves 55, 56 are one-way valves, the fluid cannot flow back through the under-pressurized pathway and thus it is forced to be delivered (arrow B).

As mentioned above, during the step of delivering the fluid (arrow B), supply station valve 11 is kept open so that new fluid can alternately enter the two sub-chambers and undesired perturbations effects would not take place while the piston is axially translating within chamber 31. Even though the new fluid entering the system during the step of delivering has not passed through actuator 70 and recirculation fluid circuit 60, it should be noted that the new fluid is not instantly delivered. In fact, the new fluid enters the sub-chamber that is under pressure, while the fluid that is delivered by the system is the one contained in the pressurized sub-chamber. Therefore, before being delivered, the new fluid is permanently moving and mixing within the respective sub-chamber thanks to the piston axial translation, thereby ensuring that the desired delivery conditions are reached before the fluid finally exiting the system.

As already mentioned above, the Applicant has found that recirculation of the fluid within chamber 31, by letting the fluid flowing through recirculation fluid circuit 60 and actuator 70 associated thereto, can remarkably reduce or even completely remove the risk of pressure pulsations when the fluid is being delivered, especially at the beginning of the fluid delivery procedure. Indeed, the fluid delivery system according to the present disclosure can properly control pressure drops or pressure spikes, occurring when piston 32 starts moving, thanks to the presence of recirculation fluid circuit 60 and actuator 70. In fact, according to the present disclosure, the fluid delivery system starts delivering the fluid (outside of the fluid delivery system) when recirculation of the fluid inside chamber 31 has already begun, therefore delivery will start when the piston is already moving inside chamber 31. This clearly means that the start of fluid delivery is not simultaneous with the start of piston movement since delivery of the fluid is started when the piston is already axially translating within chamber 31 for allowing said fluid recirculation to be performed.

Furthermore, as already mentioned above, the Applicant has also found that recirculation of the fluid within chamber 31, by letting the fluid flowing through recirculation fluid circuit 60 and actuator 70 associated thereto, can remarkably reduce or even completely eliminate the latency time of the fluid delivery system. The latency time is the technical time which the fluid delivery system inevitably requires in order to be ready to deliver the fluid. In fact, as soon as processor P instructs to deliver electric current to driving unit M, typically said electric current builds up an electromagnetic field which acts on rotor magnets that generate a torque on the gears, thereby causing the piston to start its movement. When the piston starts moving, fluid pressure starts building up and it still needs some additional time to reach and overcome the pressure threshold value which is set up for first and second outlet fluid circuit valves 55, 56. The sum of all these times is called "latency time" and it is far from being negligible, thereby inevitably causing a delay in fluid delivery out of the fluid delivery system. Thanks to the presence of recirculation fluid circuit 60 and actuator 70 associated thereto, fluid delivery system 100 of the present disclosure can overcome or reduce said latency time since, in order to perform fluid recirculation within chamber 31, piston 32 starts moving well in advance to fluid delivery.

Therefore, as soon as processor P closes actuator 70 for starting delivery the fluid (arrow B), the fluid pressure immediately increases and very quickly overcomes the pressure threshold value which is set up for first and second outlet fluid circuit valves 55, 56. Consequently, the fluid is delivered by the system very soon after processor P has ordered to start delivering.

Operation of alternative delivery system 200 shown in FIG. 2 is disclosed in detail in the following with reference to FIG. 7 and FIG. 8, said operation being substantially identical to the method steps disclosed above with reference to fluid delivery system 100 of FIG. 1.

As a first initiation step, the method of delivery according to the present disclosure comprises the step of filling first and second sub-chambers 35, 36 with the fluid to be delivered. In order to perform said filling step, processor P opens supply station valve 11, closes actuator 270 of recirculation fluid circuit 260 and acts on driving unit M for moving piston 32 within chamber 31, thereby allowing the fluid to exit supply station 10 and to flow through inlet fluid circuit 40. In detail, as soon as piston 32 is axially translated along a first direction (e.g. arrow C of FIG. 7), under pressure is generated in the first sub-chamber (e.g. sub-chamber 35) which is increasing its volume due to the piston axial movement, and the fluid flows through first inlet fluid pathway 41 and through second inlet fluid pathway 42 of inlet fluid circuit 40, through the corresponding first inlet fluid circuit valve (e.g. first inlet fluid circuit valve 45), and then it enters and fills said first sub-chamber. At the same time, the air contained within the second sub-chamber (e.g. sub-chamber 36)—which is decreasing its volume due to the piston axial movement—is primed away from the delivery system through venting means possessed by the opposite second inlet fluid circuit valve (e.g. second inlet fluid circuit valve 47). Successively, in order to fill the second sub-chamber and to prime the first sub-chamber, processor P acts on driving unit M for inverting the piston movement so that the piston is axially translated along a second direction opposite to the first direction (e.g. arrow D of FIG. 8). Since actuator 270 is kept closed while the piston is moving, under pressure is generated in the second sub-chamber (e.g. sub-chamber 36) which is increasing its volume due to the piston axial movement, and the fluid is allowed to pass through the corresponding second inlet fluid circuit valve (e.g. second inlet fluid circuit valve 47), and then to enter and fill said second sub-chamber. At the same time, the air still contained within the first sub-chamber (e.g. sub-chamber 35)—which is decreasing its volume due to the piston axial movement— is primed away from the delivery system through venting means possessed by the corresponding first inlet fluid circuit valve (e.g. first inlet fluid circuit valve 45). During the priming step some fluid exits the delivery system so that priming of outlet fluid circuit 50 is performed too.

As soon as chamber 31 is filled up with the fluid and priming of the delivery system is completed, processor P closes supply station valve 11 and opens actuator 270 of recirculation fluid circuit 260, while driving unit M is still activated and keeps piston 32 axially translating within chamber 31.

Figure 7:
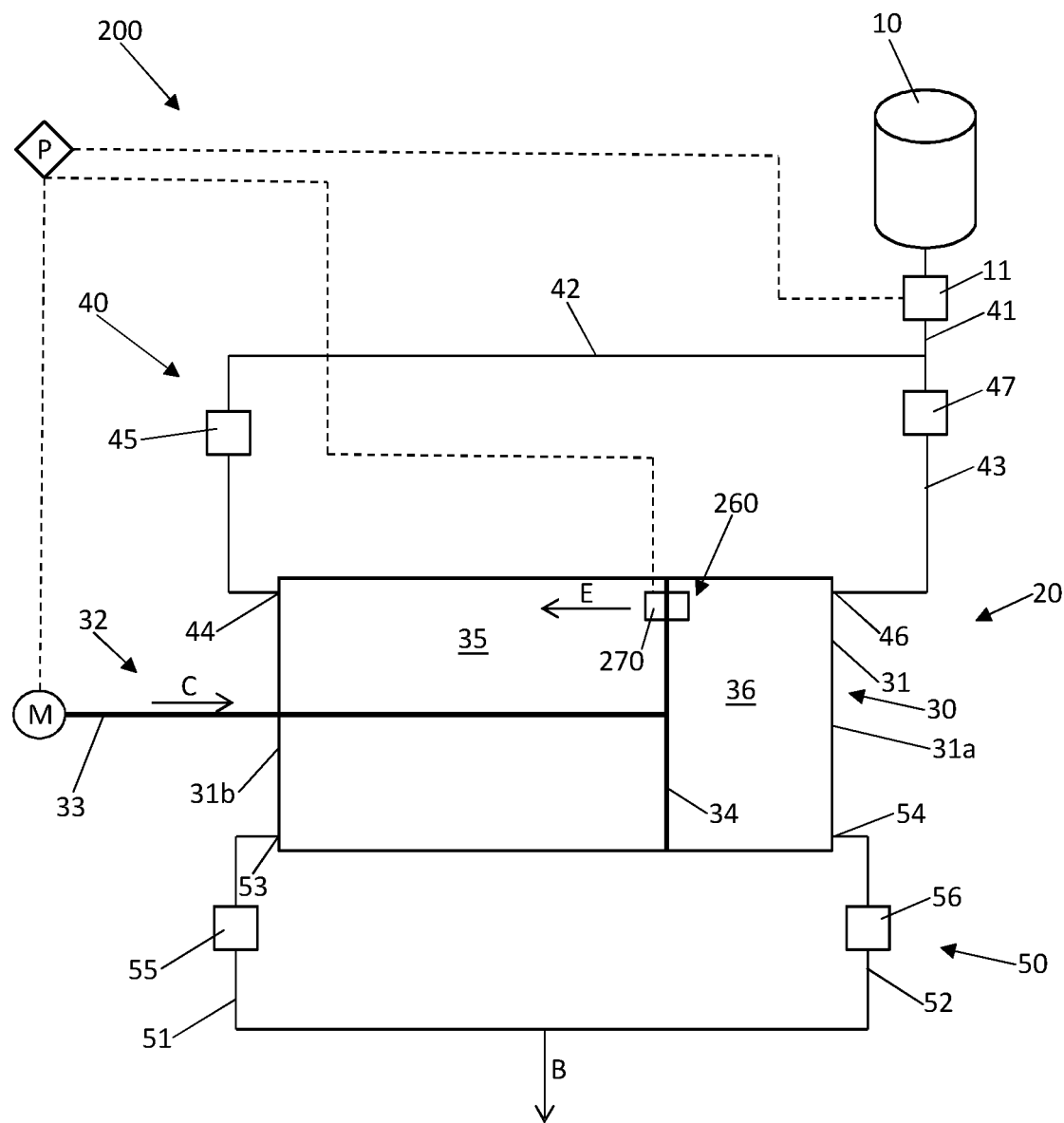

Actuator 270 is designed so that, when piston 32 is advanced in a first direction (see arrow C of FIG. 7), it allows the fluid (flowing through recirculation fluid circuit 260) to move in a second direction, opposite to first direction (see arrow E of FIG. 7). Therefore, translation of plunger 34 causes a volume increase of first sub-chamber 35 and a corresponding volume decrease of second sub-chamber 36, meanwhile the fluid initially contained within second sub-chamber 36 enters first sub-chamber 35 passing through recirculation fluid circuit 260 and actuator 270 associated thereto.

As explained above with reference to fluid delivery system 100 of FIG. 1, also in the alternative embodiment of fluid delivery system 200 of FIG. 2 the fluid contained within second sub-chamber 36 and pushed by plunger 34 is allowed neither flowing back into supply station 10 nor accessing second outlet fluid pathway 52 of outlet fluid circuit 50. In fact, both first and second inlet fluid circuit valves 45, 47 are one-way valves which allow the fluid flowing from supply station 10 into chamber 31, but not vice versa, thereby avoiding the fluid discharged from sub-chamber 36 flowing back through second and third inlet fluid pathways 42, 43 of inlet fluid circuit 40. Moreover, since second outlet fluid circuit valve 56 automatically opens only when the fluid discharged from second sub-chamber 36 has a sufficiently high pressure for overcoming the internal resilience of said valve (preferably, second outlet fluid circuit valve 56 is a ball spring-loaded check valve), when actuator 270 is in the open state the fluid discharged from second sub-chamber 36 does not have enough force to overcome the internal resilience of second outlet fluid circuit valve 56, and thus the fluid is not delivered outside of fluid delivery system 200, on the contrary the fluid discharged from second sub-chamber 36 re-fills first sub-chamber 35.

Figure 8:
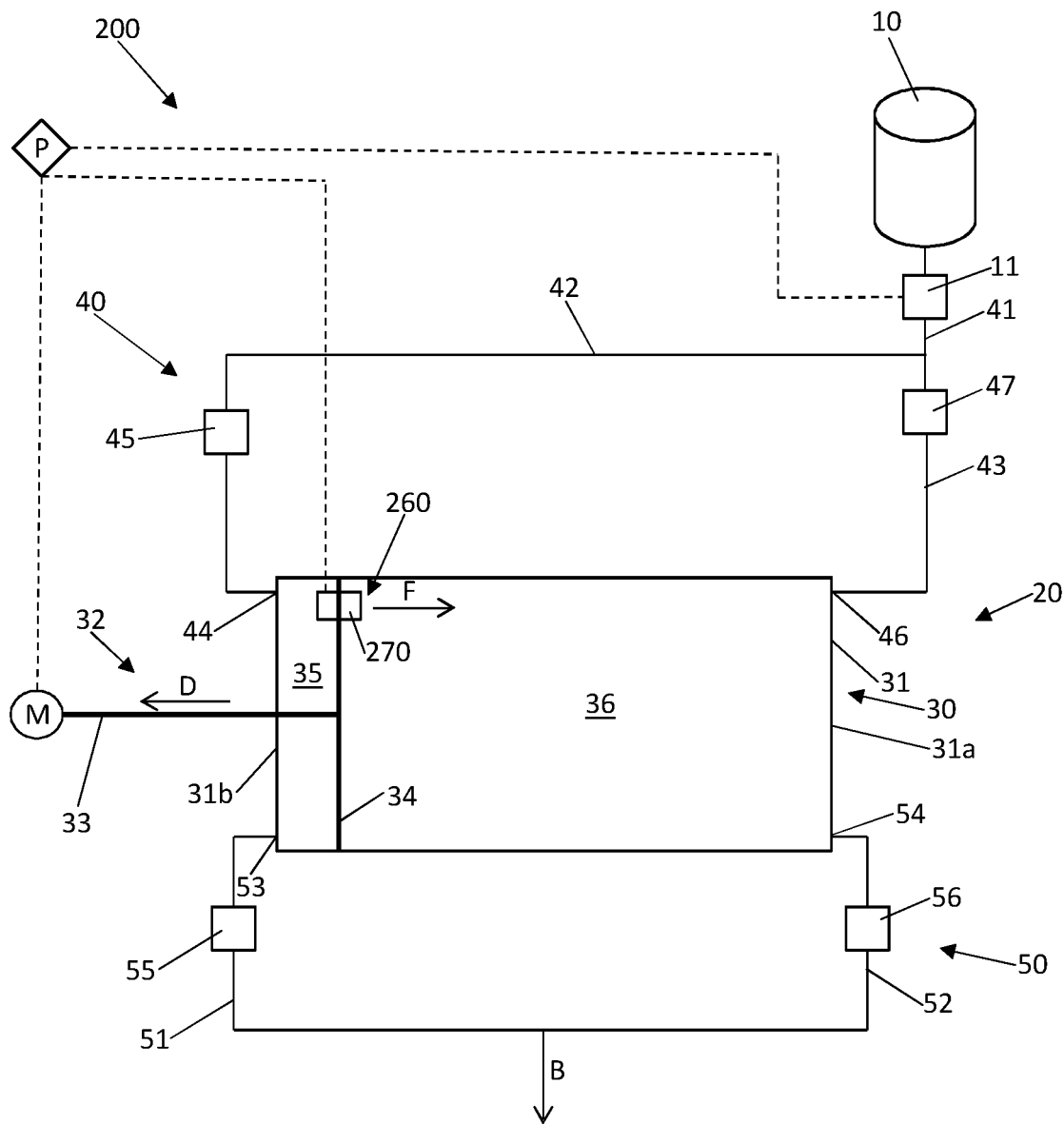

As soon as piston 32 has reached its first end-stop, i.e. plunger 34 has completed its axial translation in a first direction (right direction in FIG. 7—see arrow C) and it arrives in proximity of base wall 31a of chamber 31 so that second sub-chamber 36 contains a substantially small volume of fluid while first sub-chamber 35 contains a large volume of fluid, processor P acts on driving unit M to reverse piston axial translation (left direction in FIG. 8—see arrow D). During reverse movement of piston 32 within chamber 31 the same operative conditions mentioned above still apply, i.e. actuator 270 is kept in its open state while supply station valve 11 is kept in its closed state.

As indicated above, actuator 270 is designed so that, when piston 32 is advanced in the second direction (see arrow D of FIG. 8), it allows the fluid (flowing through recirculation fluid circuit 260) to move in first direction, opposite to second direction (see arrow F of FIG. 8). Therefore, translation of plunger 34 causes a volume increase of second sub-chamber 36 and a corresponding volume decrease of first sub-chamber 35, meanwhile the fluid initially contained within first sub-chamber 35 enters second sub-chamber 36 passing through recirculation fluid circuit 260 and actuator 270 associated thereto.

The considerations provided above with reference to piston translation in a first direction (right direction of FIG. 7—see arrow C) still apply also to piston translation in a second direction, opposite to first direction (left direction of FIG. 8—see arrow D). Therefore, the fluid contained inside first sub-chamber 35 and pushed by plunger 34 is allowed neither flowing back into supply station 10 nor accessing first outlet fluid pathway 51 of outlet fluid circuit 50. In fact, both first and second inlet fluid circuit valves 45, 47 are one-way valves which allow the fluid flowing from supply station 10 into chamber 31, but not vice versa, thereby avoiding the fluid discharged from first sub-chamber 35 flowing back through second and third inlet fluid pathways 42, 43 of inlet fluid circuit 40. Moreover, since first outlet fluid circuit valve 55 automatically opens only when the fluid discharged from first sub-chamber 35 has a sufficiently high pressure for overcoming the internal resilience of said valve (preferably, first outlet fluid circuit valve 55 is a ball spring-loaded check valve), when actuator 270 is in the open state the fluid discharged from first sub-chamber 35 does not have enough force to overcome the internal resilience of first outlet fluid circuit valve 55, and thus the fluid is not delivered outside of fluid delivery system 200, on the contrary the fluid discharged from first sub-chamber 35 re-fills second sub-chamber 36.

As soon as piston 32 has reached its second end-stop, i.e. plunger 34 has completed its axial translation in the second direction (left direction in FIG. 8—see arrow D) and it arrives in proximity of base wall 31b of chamber 31 so that first sub-chamber 35 contains a substantially small volume of fluid while second sub-chamber 36 contains a large volume of fluid, processor P acts on driving unit M to reverse again piston axial translation (right direction in FIG. 7—see arrow C), thereby starting a new charge/discharge cycle of chamber 31 of fluid delivery system 200. Of course, any number of cycles can be arranged for, said number depending on the requirements of the specific fluid to be delivered and on the requirements of the specific application where the delivery system is implemented.

The method of delivery according to the present alternative embodiment comprises the step of starting delivery (i.e. making the fluid exiting outside of the fluid delivery system) of the fluid contained within chamber 31. In order to perform said step, processor P closes actuator 270 of recirculation fluid circuit 260 and also opens supply station valve 11. During delivery of the fluid (fluid exiting the delivery system—see arrow B), supply station valve 11 is maintained in its open state because it is important to refill the sub-chambers with new fluid in order to avoid fluidic perturbations possibly impacting on the correct functioning of the piston and, consequently, of the overall delivery system. Since closing actuator 270 prevents any fluid to flow through recirculation fluid circuit 260 (while, as already mentioned above, first and second inlet fluid circuit valves 45, 47 do not allow any flow back of the fluid towards supply station 10), pushing plunger 34 in the first direction (arrow C) and in the second opposite direction (arrow D) allows the fluid to exit, respectively, second outlet port 54 and first outlet port 53. Therefore, when the fluid is pushed to pass through second outlet port 54 (arrow C), the fluid flows into second outlet fluid pathway 52 of outlet fluid circuit 50 and then it passes through second outlet fluid circuit valve 56 because at this stage of the procedure, since actuator 270 is closed, the fluid pressure is sufficiently high to overcome the internal resilience of said second outlet fluid circuit valve 56. Analogously, when the fluid is pushed to pass through first outlet port 53 (arrow D), the fluid flows into first outlet fluid pathway 51 of outlet fluid circuit 50 and then it passes through first outlet fluid circuit valve 55 because at this stage of the procedure, since actuator 270 is closed, the fluid pressure is sufficiently high to overcome the internal resilience of said first outlet fluid circuit valve 55. Therefore, the fluid is finally delivered (arrow B) by sequentially discharging it from first and second sub-chambers 35, 36.

Modifications

In order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary details. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items); the terms based on, dependent on, according to, function of (and any forms thereof) should be intended as a non-exclusive relationship (i.e., with possible further variables involved); the term a/an should be intended as one or more items (unless expressly indicated otherwise); the term means for (or any means-plus-function formulation) should be intended as any structure adapted or configured for carrying out the relevant function.

As disclosed above, the actuator of the recirculation fluid circuit and the supply station valve are both active valves controlled by processor P while the remaining valves of the fluid delivery system are check valves which do not require to be acted by processor P. According to a further embodiment (not shown in the figures), in order to enhance safety and reliability of the fluid delivery system of the present disclosure, all the valves of the fluid delivery system are active mechanical clamps that are controlled by processor P. In detail, said active mechanical clamps are mechanical gates that open/close the fluid circuit by radially acting on the external surface of the relevant tubings which form said fluid circuit.

According to an embodiment of the present invention (not shown in the figures), the volume of the supply station is remarkably greater than the volume of the chamber of the fluid delivery system. This aspect is particularly advantageous since it ensures that a high number of deliveries (e.g. of injections) can be performed without requesting frequent changes of the fluid container and, moreover, it ensures that the overall size of the fluid delivery system can be advantageously minimized, thereby making it more flexible, less cumbersome, portable (if needed) and also less expensive.

According to a further embodiment, independently from the specific fluid to be delivered, the volume of the chamber of the pump module can be sized to a minimum volume even though the volume of delivered fluid is considerably high. For instance, a delivered fluid high volume, while making use of a rather small volume chamber of said fluid, can be obtained by increasing the back and forth axial speed of the piston within said chamber.

According to a further embodiment, the method of operating the fluid delivery system of the present disclosure comprises the step of computing the amount (volume) of fluid to be delivered for a given application and, successively, the step of axially translating the piston to define a sub-chamber whose volume is substantially equal to the computed fluid volume to be delivered. This aspect is of particular interest when a low amount of fluid is requested to be delivered (i.e. lower than the chamber volume of the fluid delivery system) and thus it would be preferable to deliver such low amount while the piston is axially translating along one single direction, thereby avoiding reversal of the piston movement and possible delivery perturbations/delays related thereto.

Alternatively, the step of computing is not performed by the processor of the fluid delivery system since the computed volume to be delivered is computed off-line and provided to the processor as a delivery input data. Therefore, immediately before the step of delivery is started, the piston is axially translated to define a sub-chamber volume corresponding to said computed volume.

According to a further embodiment, the method of operating the fluid delivery system of the present disclosure comprises the step of mixing two different fluids and the step of successively delivering the obtained mixture of said two fluids. For example, the fluid delivery system of FIG. 3 comprises two supply stations that can be used for supplying two distinct fluids. In case the fluid delivery system is applied to the medical field, for example a contrast agent can be supplied from the first supply station and a saline solution can be supplied from the second supply station. Therefore, the step of filling the chamber of the pump module is performed by allowing a given amount of a first fluid (e.g. a contrast agent) to enter a first sub-chamber and a given amount of a second fluid (e.g. a saline solution) to enter a second sub-chamber. This is achieved by opening corresponding first and second supply station valves, while initially keeping the actuator of the recirculation fluid circuit in its closed working condition. Therefore, thanks to the back and forth translational movement of the piston, under pressure is alternatively generated in the first and second sub-chambers, thereby allowing the respective fluids to enter the respective sub-chambers, and also allowing priming of inlet fluid circuit, of first and second sub-chambers and of outlet fluid circuit as already disclosed above. As soon as the desired amounts of first and second fluids have entered the chamber of the pump module, the processor closes the first and second supply station valves, and it opens the actuator of the recirculation fluid circuit. Therefore, recirculation of the first fluid from the first sub-chamber into the second sub-chamber as well as recirculation of the second fluid from the second sub-chamber into the first sub-chamber (due to the inversion movement of the piston) are allowed to occur, thereby mixing the first fluid with the second fluid to finally obtain the desired mixture to be delivered. It can be pointed out that, according to this embodiment, a contrast agent at high concentration (e.g. ISOVUE®-370) can be used as a first fluid while a saline solution can be used as a second fluid, so that, by suitably mixing the highly concentrated contrast agent with the saline solution, the fluid delivery system would be able to provide volumes of contrast agent at different concentrations by starting from one single type of highly concentrated contrast agent. This is a very advantageous feature of the present disclosure since the processor (or control unit) can be programmed to calculate the volumes of the first and second fluids that are needed to be mixed for obtaining a mixture of a desired concentration which best fits with the specific patient to be treated (taking into account, for instance, his age, weight, gender, race, clinical conditions, . . . ) as well as with the specific examination to be performed (scan examination typology like CT or MR or Ultrasound, body district to be examined, . . . ).

The following are preferred aspects and embodiments of the present disclosure.

1. A fluid delivery system (100; 200; 300) comprising:
    at least one supply station (10; 310) for supplying at least one fluid;
    a pressurizing unit (20) for pressurizing said at least one fluid comprising:
        a pump module (30) comprising a chamber (31) and a piston (32) contained in said chamber, said piston having a plunger (34) that, in cooperation with internal walls of said chamber, defines first (35) and second (36) variable-volume sub-chambers, and
        a driving unit (M) connected to said piston for reciprocating the piston within said chamber;
    an inlet fluid circuit (40) in fluid communication with said at least one supply station and with said pump module for supplying said at least one fluid to said first and second variable-volume sub-chambers;
    an outlet fluid circuit (50) in fluid communication with said pump module for discharging said at least one fluid alternatively from said first and second variable-volume sub-chambers, said outlet fluid circuit being separate from said inlet fluid circuit;
    a recirculation fluid circuit (60; 260) fluidically connecting said first and second variable-volume sub-chambers, and
    an actuator (70; 270) for managing the passage of said at least one fluid in both directions between said first and second variable-volume sub-chambers, said actuator being part of said recirculation fluid circuit.
2. The fluid delivery system (100; 200; 300) according to embodiment 1, characterized in that the inlet fluid circuit (40) comprises a first inlet fluid pathway (41) which is in fluid communication with said at least one supply station (10).
3. The fluid delivery system (100; 200; 300) according to embodiment 2, characterized in that said first inlet fluid pathway (41) comprises a supply station valve (11).
4. The fluid delivery system (100; 200; 300) according to embodiment 3, characterized in that, downstream from said supply station valve (11), said inlet fluid circuit (40) comprises a second inlet fluid pathway (42) and a third inlet fluid pathway (43) which are in fluid communication respectively with said first variable-volume sub-chamber (35) and with said second variable-volume sub-chamber (36).
5. The fluid delivery system (100; 200; 300) according to embodiment 4, characterized in that said second inlet fluid pathway (42) is provided with a first inlet fluid circuit valve (45), and said third inlet fluid pathway (43) is provided with a second inlet fluid circuit valve (47).
6. The fluid delivery system (100; 200; 300) according to embodiment 1, characterized in that said outlet fluid circuit (50) comprises a first outlet fluid pathway (51) and a second outlet fluid pathway (52) which are in fluid communication respectively with said first variable-volume sub-chamber (35) and with said second variable-volume sub-chamber (36).
7. The fluid delivery system (100; 200; 300) according to embodiment 6, characterized in that said first outlet fluid pathway (51) is provided with a first outlet fluid circuit valve (55) and said second outlet fluid pathway (52) is provided with a second outlet fluid circuit valve (56).
8. The fluid delivery system (100; 300) according to embodiment 1, characterized in that said recirculation fluid circuit (60) and said actuator (70) associated thereto are external to said chamber (31).
9. The fluid delivery system (100; 300) according to embodiment 8, characterized in that said recirculation fluid circuit (60) fluidically connects, respectively, with said second inlet fluid pathway (42) downstream from said first inlet fluid circuit valve (45) and with said third inlet fluid pathway (43) downstream from said second inlet fluid circuit valve (47).
10. The fluid delivery system (200) according to embodiment 1, characterized in that said recirculation fluid circuit (60) and said actuator (270) are contained within said chamber (31).
11. The fluid delivery system (200) according to embodiment 10, characterized in that said recirculation fluid circuit (260) and said actuator (270) are integral with the plunger (34) of the piston (32).
12. The fluid delivery system (200) according to embodiment 11, characterized in that said recirculation fluid circuit (260) comprises a fluid passage obtained within the thickness of the plunger (34) for ensuring fluid communication between said first and second variable-volume sub-chambers (35, 36).
13. The fluid delivery system (100; 200; 300) according to any of the preceding embodiments, characterized in that it comprises a processor (P) which controls and actuates said actuator (70; 270).
14. The fluid delivery system (100; 200; 300) according to any of the preceding embodiments, characterized in that it comprises a processor (P) which controls and actuates said supply station valve (11).
15. The fluid delivery system (100; 200; 300) according to any of the preceding embodiments, characterized in that it comprises a processor (P) which controls and operates said driving unit (M).
16. The fluid delivery system (300) according to embodiment 1, characterized in that it comprises an additional supply station (310) and an additional supply station valve (311).
17. The fluid delivery system (100; 200; 300) according to embodiment 13, characterized in that the actuator (70; 270) and the supply station valve (11) are both active valves actuated by the processor (P).
18. The fluid delivery system (100; 200; 300) according to embodiment 13, characterized in that all the valves (70; 270; 11; 45; 47; 55; 56) of the fluid delivery system are active mechanical clamps that are actuated by the processor (P).
19. The fluid delivery system (100; 200; 300) according to any of the preceding embodiments, characterized in that the volume of the supply station (10; 310) is remarkably greater than the volume of the chamber (31) of the fluid delivery system.
20. The fluid delivery system (100; 200; 300) according to any of the preceding embodiments, characterized in that said fluid delivery system is an injection system, and said at least one fluid is a medical fluid selected from a liquid medicament, a drug or a diagnostically active contrast agent.
21. A method of operating a fluid delivery system (100; 200; 300) comprising a pressurizing unit (20) provided with a pump module (30) that comprises a chamber (31) and a piston (32) reciprocating within said chamber, said piston having a plunger (34) which, in cooperation with inner walls of said chamber, defines first and second variable-volume sub-chambers (35; 36), the fluid delivery system further comprising a recirculation fluid circuit (60; 260) and an actuator (70; 270) associated thereto for fluidically connecting said first and second variable-volume sub-chambers, said method comprising the step of operating said actuator for regulating a passage of said at least one fluid between said first and second variable-volume sub-chambers in both directions in order to balance the fluid pressure within said first and a second variable-volume sub-chambers when delivery of the fluid outside said fluid delivery system is not performed.

22. A method of operating a fluid delivery system (100; 200; 300) comprising a pressurizing unit (20) provided with a pump module (30) that comprises a chamber (31) and a piston (32) reciprocating within said chamber, said piston having a plunger (34) which, in cooperation with inner walls of said chamber, defines first and second variable-volume sub-chambers (35; 36), the fluid delivery system further comprising a recirculation fluid circuit (60; 260) and an actuator (70; 270) associated thereto for fluidically connecting said first and second variable-volume sub-chambers, said method comprising the steps of:
supplying said at least one fluid from at least one supply station (10) to said first and second variable-volume sub-chambers;
axially translating the piston within said chamber;
operating the actuator to circulate said at least one fluid from said first variable-volume sub-chamber to said second variable-volume sub-chamber through said recirculation fluid circuit, and vice versa, during multiple axial translations of the piston within the chamber, and
closing the actuator and delivering said at least one fluid out of the fluid delivery system.

23. The method of operating according to embodiment 22, wherein the step of circulating said at least one fluid between said first and second variable-volume sub-chambers (35, 36) is sequentially repeated till the step of delivering said at least one fluid out of the fluid delivery system is performed.

24. The method of operating according to embodiment 22, wherein the step of supplying comprises the step of filling said first and second variable-volume sub-chambers (35, 36) with said at least one fluid to be delivered.

25. The method of operating according to embodiment 24, wherein the step of filling comprises the steps of:
opening a supply station valve (11) associated to said at least one supply station (10);
closing the actuator (70; 270) of the recirculation fluid circuit (60; 260), and
acting on a driving unit (M) of the pressurizing unit (20) for reciprocating the piston (32) within the chamber (31).

26. The method of operating according to embodiment 24, further comprising the step of priming air outside of the fluid delivery system, said step of priming being performed simultaneously to the step of filling.

27. The method of operating according to embodiment 22, further comprising the steps of:
computing a volume of said at least one fluid to be delivered, and
axially translating the piston (32) to define a sub-chamber (35; 36) whose volume is substantially equal to the computed fluid volume to be delivered.

28. The method of operating according to embodiment 27, wherein the step of axially translating the piston (32) to define a sub-chamber (35; 36) whose volume is substantially equal to the computed fluid volume is performed immediately before the step of delivering the fluid out of the fluid delivery system.

29. The method of operating according to embodiment 22, further comprising the steps of:
providing a volume of said at least one fluid to be delivered as an input delivery data, and
axially translating the piston (32) to define a sub-chamber (35; 36) whose volume is substantially equal to the computed fluid volume to be delivered.

30. The method of operating according to any of the preceding embodiments 22 to 29, wherein said steps are governed by a processor (P) of the fluid delivery system (100; 200; 300).

31. The method of operating according to any of the preceding embodiments 22 to 30, further comprising the step of supplying a first fluid from a supply station (10) and a second fluid from an additional supply station (310), said first fluid being different from said second fluid, said first fluid being supplied to said first variable-volume sub-chamber (35) and said second fluid being supplied to said second variable-volume sub-chamber (36).

32. The method of operating according to embodiment 31, further comprising the step of mixing said first and second fluids within said first and second variable-volume sub-chambers (35; 36).

33. The method of operating according to embodiment 32, further comprising the step of delivering a mixture of said first and second fluids obtained through said step of mixing, said step of delivering being performed successively to said step of mixing.

The invention claimed is:

1. A fluid delivery system (100; 200; 300) comprising:
at least one supply station (10; 310) for supplying at least one fluid;
a pressurizing unit (20) for pressurizing said at least one fluid comprising:
a pump module (30) comprising a chamber (31) and a piston (32) contained in said chamber, said piston having a plunger (34) that, in cooperation with internal walls of said chamber, defines first (35) and second (36) variable-volume sub-chambers, and
a driving unit (M) connected to said piston for reciprocating the piston within said chamber;
an inlet fluid circuit (40) in fluid communication with said at least one supply station and with said pump module for supplying said at least one fluid to said first and second variable-volume sub-chambers;
an outlet fluid circuit (50) in fluid communication with said pump module for discharging said at least one fluid alternatively from said first and second variable-volume sub-chambers, said outlet fluid circuit being separate from said inlet fluid circuit;
a recirculation fluid circuit (60; 260) fluidically connecting said first and second variable-volume sub-chambers, and
an actuator (70; 270) for managing the passage of said at least one fluid in both directions between said first and second variable-volume sub-chambers, said actuator being part of said recirculation fluid circuit, characterized in that said recirculation fluid circuit (60) and said actuator (270) are contained within said chamber (31) and are integral with the plunger (34) of the piston (32).

2. The fluid delivery system (100; 200; 300) according to claim 1, characterized in that the inlet fluid circuit (40) comprises a first inlet fluid pathway (41) which is in fluid communication with said at least one supply station (10), said first inlet fluid pathway (41) comprising a supply station valve (11).

3. The fluid delivery system (100; 200; 300) according to claim 2, characterized in that, downstream from said supply station valve (11), said inlet fluid circuit (40) comprises a second inlet fluid pathway (42) and a third inlet fluid pathway (43) which are in fluid communication respectively with said first variable-volume sub-chamber (35) and with said second variable-volume sub-chamber (36), said second inlet fluid pathway (42) being provided with a first inlet fluid circuit valve (45), and said third inlet fluid pathway (43) being provided with a second inlet fluid circuit valve (47).

4. The fluid delivery system (100; 200; 300) according to claim 1, characterized in that said outlet fluid circuit (50) comprises a first outlet fluid pathway (51) and a second outlet fluid pathway (52) which are in fluid communication respectively with said first variable-volume sub-chamber (35) and with said second variable-volume sub-chamber (36), said first outlet fluid pathway (51) being provided with a first outlet fluid circuit valve (55) and said second outlet fluid pathway (52) being provided with a second outlet fluid circuit valve (56).

5. The fluid delivery system (200 100; 300) according to claim 3, characterized in that said recirculation fluid circuit (60) fluidically connects respectively with said second inlet fluid pathway (42) downstream from said first inlet fluid circuit valve (45) and with said third inlet fluid pathway (43) downstream from said second inlet fluid circuit valve (47).

6. The fluid delivery system (100; 200; 300) according to claim 1, characterized in that said fluid delivery system is an injection system, and said at least one fluid is a medical fluid selected from a liquid medicament, a drug or a diagnostically active contrast agent.

7. A method of operating the fluid delivery system (100; 200; 300) according to claim 1 comprising a pressurizing unit (20) provided with a pump module (30) that comprises a chamber (31) and a piston (32) reciprocating within said chamber, said piston having a plunger (34) which, in cooperation with inner walls of said chamber, defines first and second variable-volume sub-chambers (35; 36), the fluid delivery system further comprising a recirculation fluid circuit (60; 260) and an actuator (70; 270) associated thereto for fluidically connecting said first and second variable-volume sub-chambers, said method comprising the steps of:
supplying said at least one fluid from said at least one supply station (10) to said first and second variable-volume sub-chambers;
axially translating the piston within said chamber;
operating the actuator to circulate said at least one fluid from said first variable-volume sub-chamber to said second variable-volume sub-chamber through said recirculation fluid circuit, and vice versa, during multiple axial translations of the piston within the chamber, and
closing the actuator and delivering said at least one fluid out of the fluid delivery system.

8. The method of operating according to claim 7, wherein the step of circulating said at least one fluid between said first and second variable-volume sub-chambers (35, 36) is sequentially repeated till the step of delivering said at least one fluid out of the fluid delivery system is performed.

9. The method of operating according to claim 7, wherein the step of supplying comprises the step of filling said first and second variable-volume sub-chambers (35, 36) with said at least one fluid to be delivered, the step of filling further comprising the steps of:
opening a supply station valve (11) associated to said at least one supply station (10);
closing the actuator (70; 270) of the recirculation fluid circuit (60; 260), and
acting on the driving unit (M) of said pressurizing unit (20) for reciprocating the piston (32) within the chamber (31).

10. The method of operating according to claim 9, further comprising the step of priming air outside of the fluid delivery system, said step of priming being performed simultaneously to the step of filling.

11. The method of operating according to claim 7, further comprising the steps of:
computing a volume of said at least one fluid to be delivered, and
axially translating the piston (32) to define the sub-chamber (35; 36) whose volume is substantially equal to the computed fluid volume to be delivered.

12. The method of operating according to claim 7, further comprising the steps of:
providing a computed volume of said at least one fluid to be delivered as an input delivery data, and
axially translating the piston (32) to define the sub-chamber (35; 36) whose volume is substantially equal to the computed fluid volume to be delivered.

* * * * *